(12) United States Patent
Bujas et al.

(10) Patent No.: US 7,257,990 B2
(45) Date of Patent: Aug. 21, 2007

(54) ACCELERATED ULTRALOW MOISTURE PERMEATION MEASUREMENT

(75) Inventors: Roko S. Bujas, Leucadia, CA (US); Ralf Dunkel, San Diego, CA (US); William A. Raggio, Del Mar, CA (US)

(73) Assignee: General Atomics, San Diego, CA (US)

( * ) Notice: Subject to any disclaimer, the term of this patent is extended or adjusted under 35 U.S.C. 154(b) by 141 days.

(21) Appl. No.: 11/114,814

(22) Filed: Apr. 25, 2005

(65) Prior Publication Data

US 2006/0236755 A1 Oct. 26, 2006

(51) Int. Cl.
*G01N 15/08* (2006.01)
*G01M 3/02* (2006.01)

(52) U.S. Cl. ............... 73/38; 73/40; 73/40.7; 73/865.6; 73/865.8; 73/866

(58) Field of Classification Search ............. 73/865.6, 73/866, 865.8, 37–38, 40, 40.7, 46–49.8
See application file for complete search history.

(56) References Cited

U.S. PATENT DOCUMENTS

| | | | | |
|---|---|---|---|---|
| 3,126,734 A | * | 3/1964 | Stutzman | 73/40 |
| 3,286,509 A | | 11/1966 | Gluckman et al. | 73/38 |
| 3,498,110 A | | 3/1970 | Brun | |
| 3,580,067 A | | 5/1971 | Mandrell et al. | 73/159 |
| 3,590,634 A | | 7/1971 | Pasternak et al. | 73/159 |
| 3,937,649 A | | 2/1976 | Ridgely | 176/19 |
| 3,999,066 A | | 12/1976 | Osborne et al. | 250/304 |
| 4,656,865 A | | 4/1987 | Callan | |
| 4,663,969 A | | 5/1987 | Bibby et al. | 73/159 |
| 4,683,749 A | * | 8/1987 | Thurlow et al. | 73/40.7 |
| 4,965,450 A | | 10/1990 | Schiltz et al. | 250/303 |
| 5,086,642 A | * | 2/1992 | Jessel et al. | 73/1.03 |
| 5,159,829 A | | 11/1992 | Mayer et al. | 73/38 |
| 5,390,539 A | | 2/1995 | Mayer | |
| 6,119,506 A | | 9/2000 | Gibson et al. | 73/38 |
| 6,358,570 B1 | | 3/2002 | Affinito | 427/495 |
| 6,413,645 B1 | | 7/2002 | Graff et al. | 428/446 |
| 6,598,463 B2 | | 7/2003 | Sharp et al. | |
| 6,688,160 B2 | | 2/2004 | Hackett, Jr. | |
| 6,804,989 B2 | | 10/2004 | Bujas et al. | 73/38 |

(Continued)

*Primary Examiner*—Hezron Williams
*Assistant Examiner*—David A. Rogers
(74) *Attorney, Agent, or Firm*—Fitch, Even, Tabin & Flannery

(57) ABSTRACT

By measuring ultralow moisture permeation through a barrier material sample at a temperature substantially above ambient, definitive values are produced on an accelerated basis that can be used to accurately predict long term daily performance of that barrier material. The sample is heated to a desired test temperature where there is controlled access to both its upstream and downstream surfaces, and HTO vapor is then supplied at predetermined relative humidity to the upstream surface by fracturing a glass ampoule containing not more than 10 millicuries of specific radioactivity for each test. Radioactive gas permeating from the downstream surface is collected by circulating a very slow flow of dry carrier gas past the downstream surface, which stream flows to an ionization chamber containing a beta-particle radiation monitor. Continuous monitoring generates signals that are converted to calculate instantaneous permeation rates through the sample, and operation at such elevated temperature is carried out until the values being monitored reach a steady state, allowing accurate prediction of the extent of long term barrier protection against moisture permeation the sample will exhibit.

17 Claims, 3 Drawing Sheets

U.S. PATENT DOCUMENTS

| | | | |
|---|---|---|---|
| 6,966,216 B2 * | 11/2005 | Hotta | 73/49.3 |
| 2002/0152800 A1 | 10/2002 | Bouten et al. | |
| 2003/0074954 A1 | 4/2003 | Engle et al. | 73/38 |

* cited by examiner

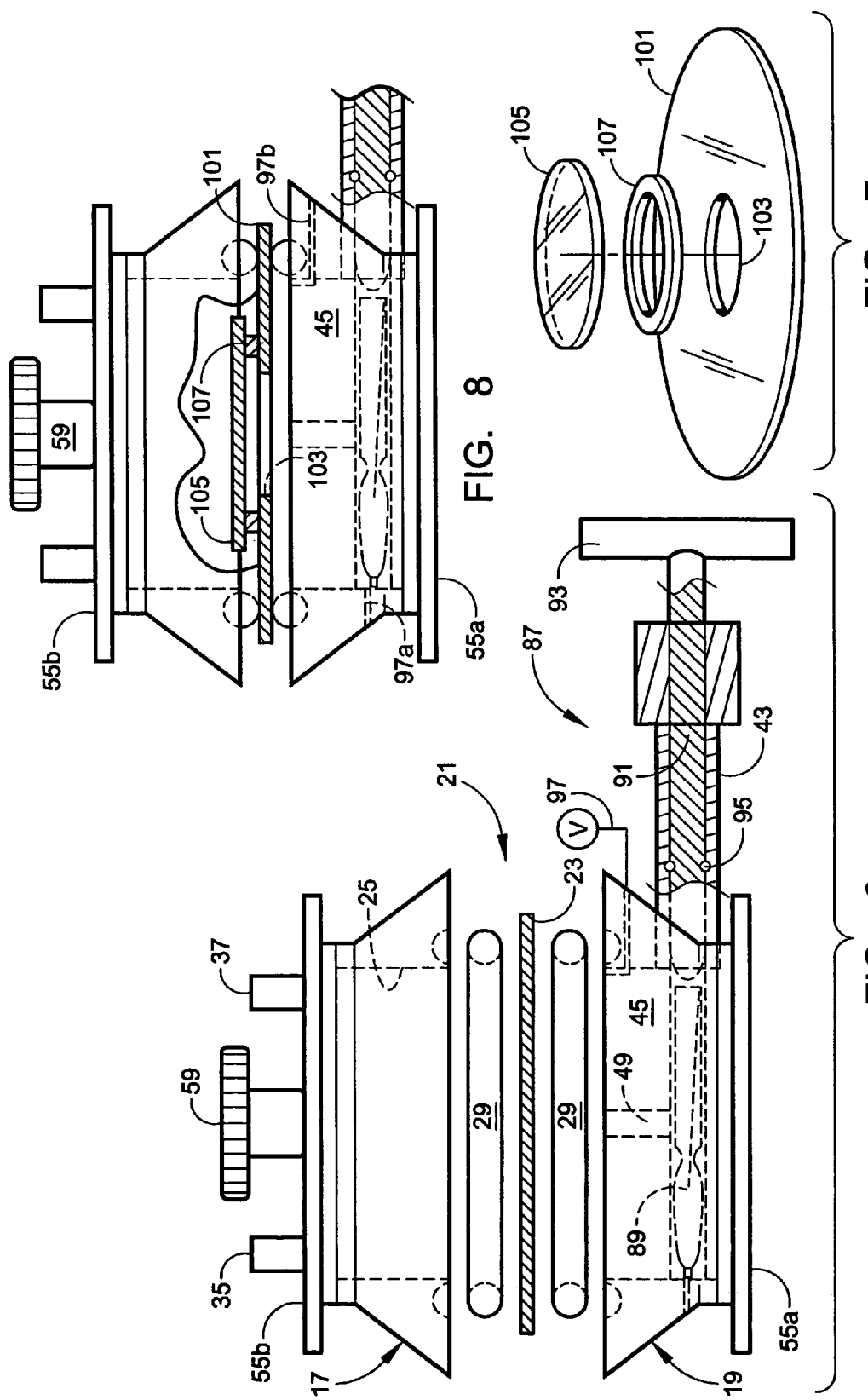

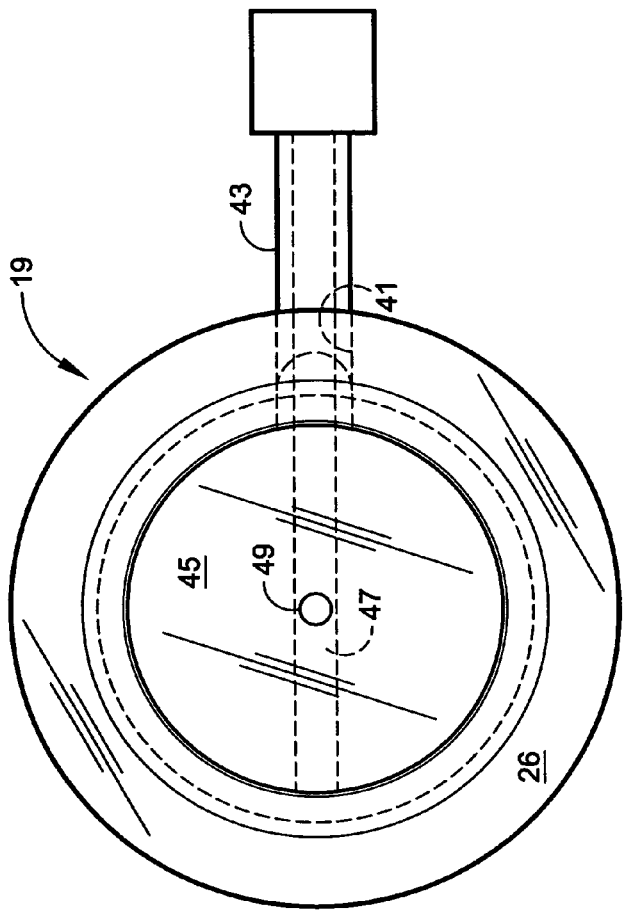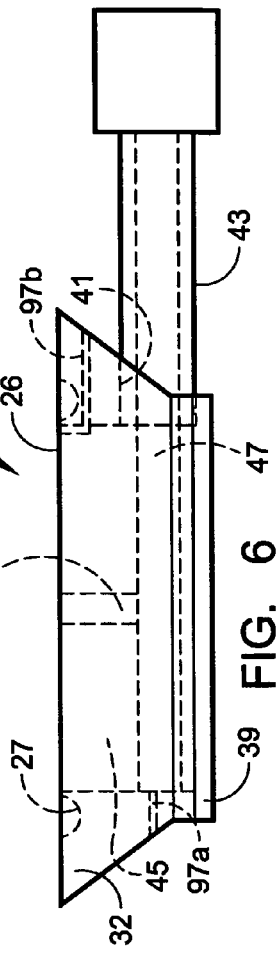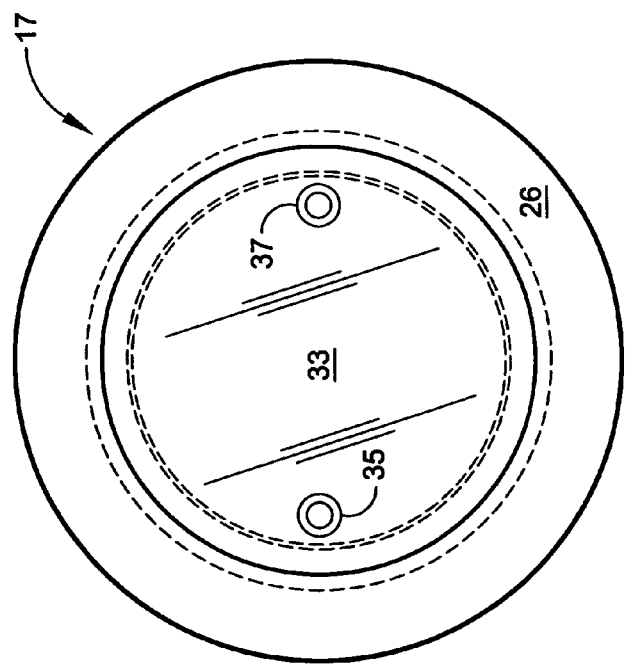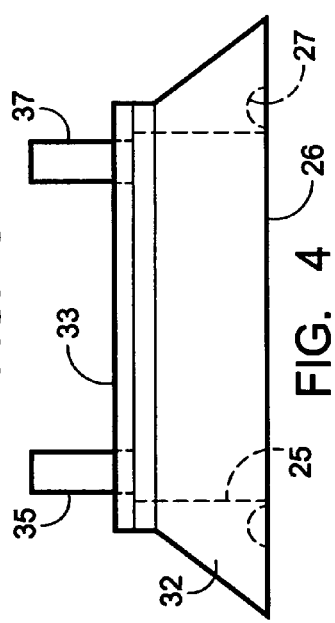

ACCELERATED ULTRALOW MOISTURE PERMEATION MEASUREMENT

This invention was made with Government support under Army Contract No. DAAD19-02-3-0001. The Government may have certain rights in this invention.

FIELD OF THE INVENTION

The invention relates to methods and apparatus for measurement of extremely low rates of permeation of moisture, and more particularly to methods and apparatus for safely and efficiently measuring an ultralow moisture permeation rate through an object, such as a sample composite polymeric film which carries a barrier coating, on an accelerated basis.

BACKGROUND OF THE INVENTION

With the development of better and better barrier materials, generally composites that include a plastic film base, it has now become very desirable to be able to precisely measure the rate of permeation through such barrier materials in order to properly evaluate them. As barrier materials have improved in their resistance to moisture and oxygen permeation, it has become clear that better, more sophisticated methods and apparatus will be required to be able to accurately measure such lower and lower rates of permeation that are expected to be representative of barrier materials that are felt to be needed for commercial applications.

Gas permeability measuring devices have generally been known in this art, some of which were developed to serve the garment industry where the production of fabrics that were highly resistant to water permeation were being developed. However, more recently, with the development of LCD's, LED's and OLED's, it has become important to develop barrier materials that have an extremely high resistance to moisture permeation and oxygen permeation; it has been scientifically shown that there is a relationship between the permeation of moisture and the permeation of oxygen through a barrier so that, by measuring moisture permeation rate, a reasonable assessment can also be obtained for the resistance of the barrier film to the permeation of oxygen.

Products in various electronics fields, such as OLED's and LCD's, and certain pharmaceuticals are among the products for which it is presently felt to be particularly important to minimize exposure to oxygen and moisture in order to resist deterioration of such products. Barrier materials that have been developed to protect such materials generally include multilayer composites made of polymeric films and thin layer inorganic materials, and the search goes on for providing increasingly better multilayer, thin film barrier materials for this purpose. These materials will generally include a thin polymeric film, e.g. PET, that will carry at least one overall inorganic layer. For example U.S. Pat. No. 6,413,645 entitled "Ultrabarrier Substrates" describes the problem and the search for more permeation-resistant materials. However, this patent states that oxygen and water vapor transmission rates even as high as 0.005 cc or $gm/m^2$/day are below the detection limit of current industrial instrumentation. U.S. application No. 2004/0209126 discloses a highly effective barrier film wherein a PET film having barrier coatings of ITO and/or $SiO_2$ is deposited thereupon. By using a specific, ion-assisted, sputtering or evaporation process, the result is an improved structure that exceeds the performance of comparable flexible films.

To measure moisture permeation, U.S. Pat. No. 3,580,067, at an early date used the amount of change in weight of a suitable desiccant in a closed container. U.S. Pat. No. 4,663,969 later disclosed apparatus for testing water vapor transmission which employed a heated water bath and measured the change of solute indicative of moisture permeation by measuring a change in electrical conductivity.

Our U.S. Pat. No. 6,804,989 (Oct. 19, 2004) discloses an apparatus for measuring ultralow water permeation through a composite barrier film that includes a thin polymer layer by utilizing a radioactive gas, such as tritiated water vapor (HTO) or carbon$^{14}$monoxide ($^{14}$CO). The sample is mounted to provide controlled access to opposite surfaces of the barrier film, and HTO or $^{14}$CO is supplied to its upstream surface. The permeating radioactive gas is collected in a carefully controlled, dry, carrier gas stream and monitored in a manner to precisely determine even extremely low permeation rates through the sample. The method affords highly accurate measurement of ultralow permeation rates by uniformly controlling the humidity (or CO concentration) at the upstream surface and by using a controlled, very low flow of dry carrier gas, preferably having a matching molecular weight, to collect all the radioactive, permeated gas and carry it to a radiation monitor in an ionization chamber where the permeation rate is then calculated.

Although the last described apparatus is able to effectively evaluate the performance of the highly effective barriers involved, there is an inherent need to provide test data for resistance to moisture permeation over long time periods. Although continuous testing for such long periods of time can supply such data, it is undesirable to have to wait until the end of perhaps a year or even 1 month of such testing. The present desire to shorten the time needed to determine a material's extended resistance to moisture permeation has caused the industry to turn to testing for moisture permeation at elevated temperatures. However, testing for such short times at high temperatures has really been used as only a pass/fail test as no definitive data has been generated as a part of such testing. Thus, more accurate apparatus and methods continue to be sought to provide accelerated testing that can provide a reasonably accurate indication of a material's long term barrier properties at ambient temperature in the form of definitive values.

SUMMARY OF THE INVENTION

It has now been found that an accelerated test method can be provided for measuring ultralow moisture permeation through a barrier material sample using a temperature substantially above ambient which produces definitive values than can be used to accurately predict daily performance of that barrier material after at least one month or more.

The sample through which permeation is to be measured is heated to a desired test temperature, e.g. 85° C., in an enclosure where there is controlled access to both its upstream surface and its downstream surface. A radioactive gas is then supplied at predetermined relative humidity to the upstream surface of the sample, and radioactive gas permeating from the downstream surface is collected by circulating a very slow flow of dry carrier gas past the downstream surface. Tritiated water vapor (HTO) is advantageously used as the radioactive gas. The radioactive stream flows to an ionization chamber containing a beta-particle radiation monitor, and continuous monitoring to detect the presence of beta-particle radiation generates signals that are converted to calculate instantaneous permeation rates through the sample. The sensitivity of the test components is sufficiently high that there is a capablity of detecting values that are equivalent to permeation of moisture at a rate of $1\times10^{-6}$ gm/m$^2$/day or less. Continued operation at an elevated temperature of about 85° C. is carried out until the values being monitored reach a steady state, usually after a period of about 2-7 days. Achievement of this steady-state level allows accurate prediction of the extent of barrier protection against moisture permeation the sample will exhibit after one month or more. Based upon such an accepted value, a reasonable prediction can be made for barrier performance over one year or more.

There is also provided apparatus for carrying out the above method which comprises means for heating a sample to a test temperature substantially above ambient and for mounting the sample at the test temperature so as to provide controlled access to upstream and downstream surfaces of the sample via chambers that are also being heated. The apparatus has provision for supplying a minute but adequate amount of a radioactive gas to an upstream chamber where it will contact the upstream surface of the sample at a controlled relative humidity, and for circulating a very slow flow of carrier gas through the other chamber to collect the gas permeating from the downstream surface of the sample. A conduit directs the stream exiting from the downstream chamber to an ionization chamber containing a radiation monitor as mentioned above.

The apparatus can be operated under a standard laboratory exhaust hood and requires no elaborate safety precautions because the amount of HTO is minimized so that a specific radioactivity of more than 10 millicuries is never present at one time. This desirable objective is attained by supplying only a minute quantity of the radioactive material in a sealed receptacle. Provision is made to first remove all humidity from the chamber prior to supplying HTO vapor, the minute amount of which vapor is then supplied for each separate test by fracturing a small glass ampoule containing the precise amount. Provision is also made to resize the upstream chamber to assure the desired RH and balance the pressure with the downstream pressure to avoid any significant pressure differential therebetween.

BRIEF DESCRIPTION OF THE DRAWINGS

FIG. 2 is an exploded perspective view of the mounting device shown in FIG. 1.

FIG. 3 is an enlarged top view of the upper portion of the device of FIG. 2.

FIG. 4 is a front elevation view of the upper portion of the device shown in FIG. 3.

FIG. 5 is a top view of the lower portion of the device shown in FIG. 2.

FIG. 6 is a front elevation view of the lower portion shown in FIG. 5.

FIG. 7 is an exploded perspective view of a alternative test sample.

FIG. 8 is a partial schematic view that shows the alternative test sample of FIG. 7 mounted in the mounting device illustrated in FIG. 2.

DETAILED DESCRIPTION OF THE PREFERRED EMBODIMENTS

Figures 1, 1A:
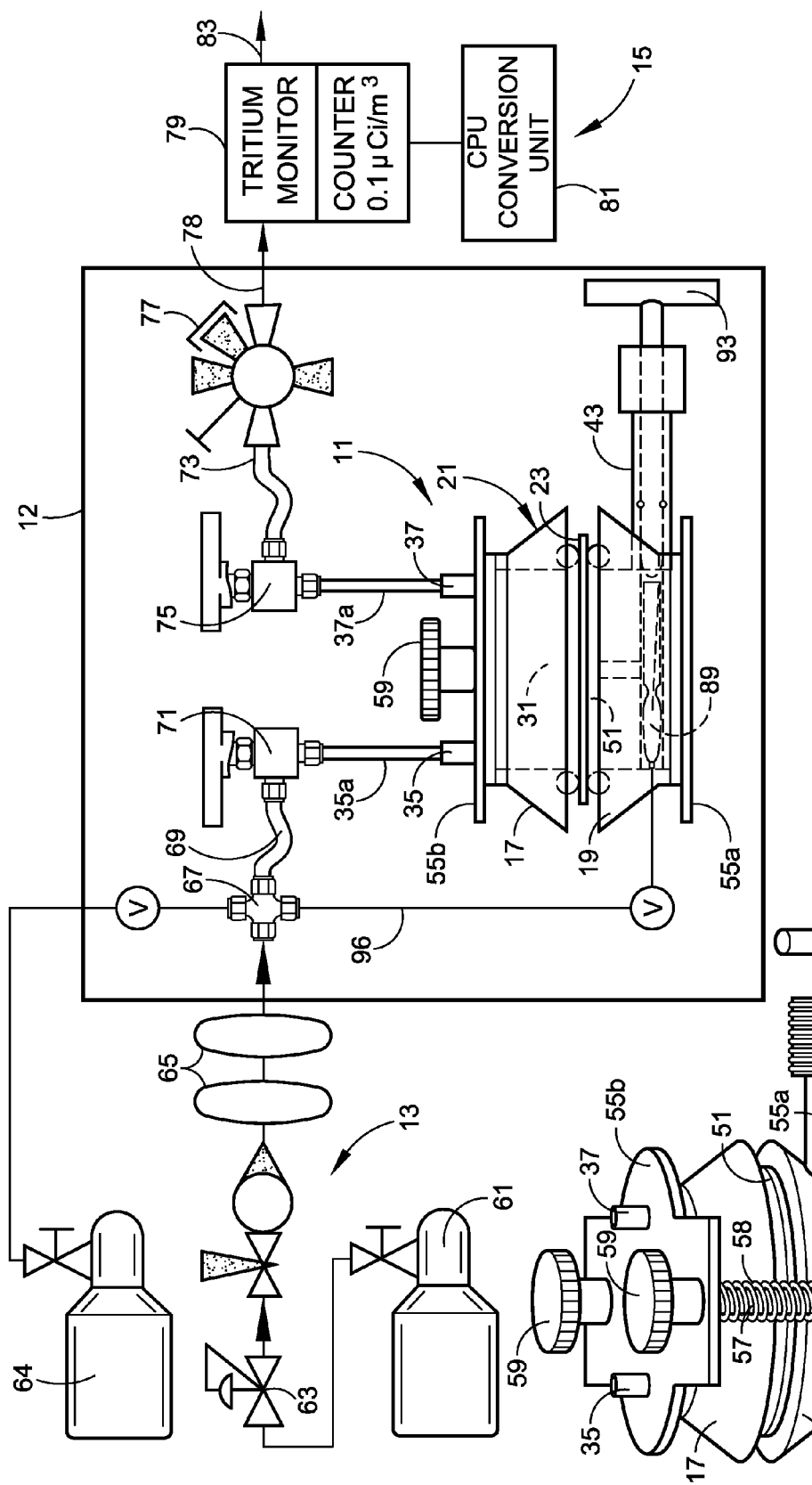
FIG. 1 is a schematic drawing showing apparatus for measuring ultralow rates of gaseous permeation through a sample at an elevated temperature, which apparatus embodies various features of the invention.
FIG. 1A is a perspective view, reduced in size, showing the mounting device illustrated in FIG. 1.

The invention provides a method and apparatus for accurately measuring ultralow moisture permeation through a thin film composite or other material having very good barrier properties, i.e. high resistance to such penetration. As earlier mentioned, there has been substantial development of new barrier materials, generally thin film composites, which provide high moisture and oxygen resistance for use as barriers for LCD's, LED's and OLED's that require such barrier protection to assure long term performance, particularly for the cathode components thereof which are frequently manufactured of calcium and are particularly susceptible to degradation from moisture and attack by oxygen.

The apparatus shown in FIG. 1 includes a mounting device 11 where a sample object for which permeation is to be measured is appropriately mounted so that a flat region of precise surface area will have its upstream surface directly exposed to an atmosphere of uniform composition; this facilitates monitoring and accurately calculating permeation through the sample. Although the illustrated embodiment of the device 11 is designed to measure permeation through a thin film or a comparable generally flat object, similar mounting devices could be constructed to handle similar objects of different shape. The mounting device 11 is disposed within a temperature-controlled oven 12 and is heated to the desired test temperature.

Associated with the mounting device 11 is a system 13 for supplying a controlled atmosphere downstream of the sample being tested, and also for purging the region upstream of the sample. There is also provided a system 15 for monitoring the beta-particle radioactivity of a gaseous stream exiting the device 11 and for interpreting the signals generated to calculate the permeation rate through the film or other sample at that instant and/or over a period of time. The arrangement is such that the overall sensitivity is sufficient to detect and measure permeation rates of moisture as low as $10^{-6}$ to $10^{-7}$ gm/m$^2$/day.

The illustrated mounting device 11 includes upper and lower parts or portions 17, 19. These two parts interface with each other to provide a central receptacle 21, which in the illustrated device is a generally cylindrical region designed for the mounting of a flat, thin sample 23 or other such test element for which a permeation characteristic is to be determined. The central receptacle 21 is mainly provided by a cavity 25 in the undersurface of the upper part 17; this cavity is cylindrical and may, e.g., have a depth of about 25 mm and a diameter of about 60 mm. The upper part 17 and the lower part 19 have facing flat annular surfaces 26, in each of which is formed an arcuate groove 27 of semicircular cross section; each groove accommodates a sealing or O-ring 29 of resilient material that extends past the respective flat surface. When the O-rings 29 are placed in each of these grooves 27 and the upper and lower parts 17, 19 are clamped or otherwise pressed together with a sample 23 in place, the O-rings 29 seal against the sample thin film 23 through which permeation is to be measured and define the surface area that will be exposed to the controlled atmosphere. The flat film thus closes the bottom of the cavity 25 and creates a downstream chamber 31 through which carrier gas is to be circulated.

To minimize the costs of manufacturing the prototype shown in the drawings, similar bodies 32 were created that could then be respectively altered to create the upper part 17 and the lower part 19 that are shown. To avoid potential radioactivity contamination, the parts were made of glass which could be thoroughly cleaned. As known in this art, it is also possible to mold the parts from appropriate polymeric materials, and of course, they could be machined from metal. The facing flange portions of both the upper and lower parts are thus the same having the same size flat surface 26 and semi-circular groove 27; having two parts of the same diameter facilitates alignment when mounting a sample therebetween. The body 32 of the upper part 17 has its upper surface sealed by a circular flat plate 33 that carries a short inlet tube 35 and outlet tube 37 to provide communication to and from the downstream chamber 31 when a sample 23 is being tested. The body 32 of the lower part has its bottom sealed by a similar circular glass plate 39, and a side inlet 41 is suitably cut in its sidewall at the bottom. A side conduit 43 is fixed in the side inlet so as to provide a passageway leading into the bottom portion of the lower part 19. The central cavity of the lower part 19 is filled with a glass insert 45 that is suitably sealed in place. The insert 45 includes a diametrically aligned bore 47 that extends across the insert and is aligned with the side conduit 43 passageway; it also includes an axial passageway 49 that extends upward from the bore to a flat upper face. When the sample 25 is clamped in test position, it becomes seated a short distance above the flat upper face of the insert 45, as determined by the thickness of the O-ring 29, and this region forms a portion of what constitutes an upstream chamber 51 which includes the volume of the axial passageway 49 and a portion of the volume of the diametrical bore 47, as explained hereinafter.

As best seen in FIG. 1, the upper and lower parts 17, 19 are mounted between a pair of parallel horizontal plates 55a and b. The lower or base plate 55a, to which the lower part may be suitably affixed if desired, carries a pair of upstanding posts 57 which are slidably received in apertures in the upper plate 55b to which the top surface of the upper part is preferably affixed with the inlet and outlet tubes 35, 37 passing through this plate. The upper ends of the posts 57 are threaded, and the posts carry compression springs 58 that are sized so as to maintain the upper and lower parts slightly spread apart. Handwheels 59 are threadably received on the threaded upper ends of the posts, and by simultaneously turning the two handwheels, the upper part 17 can be forced downward so as to clamp a flat sample 23 between the pair of aligned O-rings 29.

The overall gas supply system 13, illustrated in FIG. 1, includes systems for purging the atmosphere in the upstream chamber 51 and for supplying a flow of dry gas through the downstream subchamber 31 to collect the HTO that permeates through the sample 23 being tested. The overall gas supply system 13 includes a tank 61 of gas under pressure, and the usual pressure regulator 63 to supply a carrier gas at a desired, appropriate pressure. Although various dry gases might be used, including argon, nitrogen, methane and dry air, it has been found that methane and argon have superior properties in an ionization chamber. For measuring moisture permeation, methane is preferred because the molecular weight of methane is very close to the molecular weight of water, as a result of which any potential stratification in the downstream chamber at a low flow of gas therethrough is positively avoided. A test device such as this utilizing HTO, for general safety considerations, should be operated under a standard laboratory hood, and the oven 12 would be so located below a hood. If methane is employed, the tank 61 would normally also be located under the hood. A second cylinder 64 of argon is desirably also provided, with a suitable valve arrangement to allow selection of either one or both gases to purge the upstream and/or the downstream chambers prior to beginning the actual test procedure. Ultradry methane at a tank pressure of 2500 psi may be fed through the pressure regulator 63 to reduce its pressure to about 15 to 20 psia (i.e. just slightly above atmospheric pressure) for the testing/monitoring purposes of this invention. It is preferably passed first through a desiccant dryer 65 to remove any possible moisture that might be present and thus assure its ultradry condition.

The flow of methane leaving the desiccant dryer 65 enters a 4-way crossover connector 67, one leg 69 of which leads through a small ball valve 71 to a flexible conduit 35a connected to the inlet tube 35 leading to the downstream chamber 31. An exit conduit 73 containing a ball valve 75 is similarly connected by flexible tubing 37a to the outlet tube 37 from the chamber 31; the exit conduit 73 leads to the monitoring system 15. During normal testing, both of the ball valves 71, 75 are open, and a slow flow of carrier gas is maintained into the chamber 31 through tube 35, past the sample film 23 being tested, and out through the outlet tube 37 to the monitoring system 15, which includes a monitoring chamber 79 that contains a beta-particle monitor, e.g. a commercial component that is disposed in a cylindrical chamber of small volume, i.e., preferably not greater than about 2 liters. Tritium emits beta particles, and an ionization detector, such as the Model 224 available from femto-TLCH, INC. of Carlisle, Ohio, in such a small chamber will effectively monitor very minor amounts of radioactivity exhibited by the permeated tritium in this test apparatus. It has been found that the use of a very low flow of carrier gas, e.g. about 1 L of dry methane per hour, in combination with a small volume, radiation-monitoring chamber, e.g. about 2 liters, will provide sufficient sensitivity to be able to achieve measurement levels of HTO permeating through a sample of about 50 to 100 $cm^2$ that are equivalent to as low as about $10^{-6}$ to $10^{-7}$ $gm/m^2/day$.

The ionization detector in the chamber 79 creates signals in response to the change in ionization current being measured which results from the beta particles emitted by the tritium in HTO vapor that has permeated through the sample and sends these signals to an interconnected counter which in turn sends signals to a CPU conversion unit 81. Such a detector in this small volume, cylindrical chamber is effective to detect an amount of specific radioactivity as low as about 0.1 microcurie per $m^3$, and the size of the chamber is a very small fraction of a cubic meter. Signal processing is further described hereinbelow. An outlet 83 from the opposite or exit end of the cylindrical radiation monitoring chamber 79 can simply be vented through the safety hood, as the potential amount of HTO in the stream will be well below tolerable limits.

An HTO supply subsystem 87 is provided which utilizes the passageway in the side conduit 43 and the interconnected passageways 47 and 49 that are formed in the insert 45 in the lower part 19 of the mounting device, all of which form portions of the upstream chamber 51.

The passageway through the side conduit 43 and the diametrical bore 47 in the insert 45 provide a subchamber of the upstream chamber 51, into which a frangible glass ampoule 89 containing a precise amount of HTO is slideably inserted using a pusher or plunger 91 which has a handle 93 at its proximal end. The plunger 91 carries one or more O-rings 95 that provide a tight fluid seal between the plunger and the interior cylindrical wall of the side conduit 43. A new glass ampoule 89 is used for each test, and the ampoule contains 0.01 to 0.001 ml of HTO which will have a specific radioactivity of not more than 10 millicuries, and preferably between about 0.1 and 1 millicurie. This minute amount of HTO is conveniently supplied by use of a short length of capillary tubing into which the HTO is drawn, with the length of capillary tubing being inserted into a glass ampoule which has been evacuated and/or flushed with dry argon or the like and then promptly sealed as by melting a tip at one end. The volume of the upstream chamber 51 will consist of volume below the surface of the flat sample 23 in the region between the lower O-ring 29 and the flat upper surface of the insert 45, the axial passageway 49, and the portion of the diametrical bore 47 in the insert that is not occupied by the distal end of the plunger 91. As pointed out hereinafter, the plunger 91 is positioned at a predetermined location so as to provide a precise volume for this upstream chamber and a pressure substantially equal to the pressure of the carrier gas in the downstream chamber so that there will not be any significant pressure differential between the upstream and downstream chambers during the test. Knowing this volume, the release of, e.g. 0.001 ml of, HTO vapor from the glass ampoule 89 will assure a 100% relative humidity when the test is ready to begin at the desired temperature, e.g. 85° C.

Because only one glass ampoule is present at any one time, and because the glass ampoule contains an amount of specific radioactivity not greater than 10 millicuries, the health hazard is so minimal, that the entire test can be simply operated under a standard laboratory hood that will exhaust to the roof of the building or the like without the need for additional precautions, which is a substantial advantage when handling tritium. Moreover the amount of HTO in view of the fact that the expected permeation will be usually less than 0.001 gm/sq.m/day and the area of the sample for the test will likely be in the neighborhood of 50 sq.cm, e.g. about 10 to 100 sq. cm, there should be negligible loss of humidity over the usual test period, i.e. 2-7 days. So, if the ampoule and chamber are sized such that initial RH is preferably initially about 100%, the RH will remain at essentially 100%, i.e. greater than/about 98% RH, throughout the test.

A valved conduit 96 leads from the crossover 67 to the subchamber on the upstream side of the sample which serves as a holder for the glass ampoule 89; entry is provided via a small purge inlet 97$a$ (FIG. 6). This arrangement is provided for purging the entire upstream chamber 51 of any humidity before a test is begun by flow therethrough and out a valved exit conduit 97$b$ (FIG. 2).

The radiation monitor 79 is electrically connected to the conversion unit 81 which includes a CPU that is programmed to make calculations, from the signals received from the radioactivity monitor, to show a calculated value in terms of the instantaneous rate of permeation of moisture; this value is based upon the assessment of the amount of HTO collected and carried by the flowing methane gas. From such readings accumulated over periods of time and knowledge of the rate of gas flow, the unit 81 can be programmed to report an instantaneous value in terms of the amount of water per square meter per day which is permeating through the sample 23 being tested which is being exposed to a controlled humidity under the elevated temperature, or alternatively to provide a cumulative readout in the form of the total amount permeated since the start of the test.

As an example of the overall test operation, an appropriately sized sample 23 of a barrier film to be tested is carefully installed in the mounting device 11 so that it rests upon O-ring 29 carried by the upper surface of the of the lower part 19 of the device. The upper half 17 is then carefully lowered in place so that it is supported on the springs 58, with the O-ring 29 carried by the upper part located just above the upper surface of the sample to be tested. The oven 12 is closed, and the mounting device 11 with the thin film sample 23 in place is heated to a test temperature at least about twice ambient, e.g. to about 85° C. This allows this thin film, which will usually have at least one inorganic coating covering at least one surface thereof to equilibrate before being tightly restrained. Then, the handwheels 59 installed on the posts are tightened so as to clamp the film 23 securely between the mating sealing rings 29, thereby closing the upper and lower chambers 31 and 51. Once the mounting device is closed, a slow flow of dry argon (Ar) or argon mixed with methane is passed through the upstream chamber 31 to purge it of humidity by opening the valve in the line 96. Purge flow is through the side inlet 97$a$ into the diametrical bore 47 near the ampoule 89, through the axial passageway 49 and into the region just below the sample, exiting via a valved purge side outlet 97$b$. Following this purging, a purge flow of dry methane (or $CH_4$ plus Ar) is sent through the downstream chamber 31 to rid that chamber of any humidity and residuals of a radioactive nature; such flow is directed through the radiation monitoring chamber and continued until a stable baseline is recorded which indicates the chamber has been completely purged.

When the test is ready to begin, the plunger 91 is sharply rapped to fracture the glass ampoule 89, causing $HTO/H_2O$ vapor to flow throughout the upstream chamber 51. The upstream chamber 51 is quickly filled with a uniform humidity in a matter of minutes. The plunger 91 is withdrawn to a predetermined position to precisely size the overall chamber 51 so that the $HTO/H_2O$ in the ampoule provides the desired RH, usually about 85 to 100% RH, at 85° C. and to establish a pressure that will be substantially equal to the carrier gas pressure, e.g. about 15 to 20 psia, in the downstream chamber, so that there will be no significant pressure differential between the upstream and the downstream chambers. The thin polymeric film layer 23 fairly rapidly saturates with $HTO/H_2O$. At this time, a slow uniform flow of dry methane is passed through the downstream chamber 31 and continued at a rate of about 1 liter/hour. When it is noticed that some radiation above baseline is being detected, the test is considered to have begun. Such a slow flow of dry methane at, for example, about 1 liter per hour is continuously maintained through the downstream subchamber 31 and then out through the radiation monitor 79. If desired, a volumetric flow monitor (not shown) may be included to assure precision is being achieved. The signals generated by the counter at the radiation monitor 79, for the duration of the test, are continuously fed to the conversion unit 81 which is programmed to calculate a moisture permeation rate in desired terms, as for example, grams of water per square meter of surface area per day. The unit 81 will indicate the current or instantaneous permeation rate being detected as well as provide a cumulative graph showing the change in these values over the entire length of the test at 85° C. Assuming, for example, that both chambers are balanced at 18 psia and that the upstream chamber is at about 99% RH at beginning of test, after about 3 days operation, the pressure on the upstream side may have dropped. As a result of cumulative data that is being collected, the amount of $HTO/H_2O$ that has permeated through the sample can be calculated. Based upon the calculated amount of vapor that has been withdrawn, the decrease in pressure in the upstream chamber 51 is then calculated; in turn, the movement of the plunger 91 to compensate for the decrease is calculated. Then adjustment is made by moving the plunger inward to decrease the volume and thus return the pressure of the chamber 51 to 18 psia. After a period of 2 to 7 days, the rates that are being monitored are being continuously recorded will begin to level out as a steady state is reached, where the value is not changing by more than about ±5% which signals the usual end of the test.

The steady-state value at such an elevated temperature, e.g. about 85° C., provides an accurate indication of the performance of the sample as an effective barrier to moisture permeation for one month or longer at ambient temperature. Moreover, this test result allows the reasonable prediction of the barrier performance of the sample for a year or more and thereby allows a manufacturer to determine the amount of desiccant that should be incorporated in a device being protected by such barrier material (or by the perimeter seal to be described hereinafter).

Once the test has been satisfactorily completed, the mounting device 11 can be opened, and the sample 23 and the broken glass ampoule removed. The minute amount of HTO that was distributed throughout the atmosphere in the upstream chamber can be safely allowed to vent through a standard laboratory hood. The sample 23 is then replaced with the next one to be tested, and a new ampoule is inserted before the above-described procedure is repeated.

Shown in FIGS. 7 and 8 is an arrangement for testing a different type of sample for moisture permeation using the system and apparatus of FIG. 1. Glass plates have long been used as protection for OLEDs and the like, as glass is an excellent barrier to both oxygen and moisture. In many cell phones, for example, two thin glass plates are used to sandwich an OLED or other light-emitting display. However, in such an arrangement, a perimeter seal is necessary to prevent moisture and oxygen from otherwise entering from the side edges of the assembled arrangement. As a result, it has become important to be able to determine the effectiveness of a perimeter seal, which will normally be a line or bead of adhesive that completely encircles the usually rectangular perimeter of the device. Whereas the thickness of the seal is determined by the thickness of the light-emitting display material being sandwiched between the two plates, the width of the line of adhesive is variable, as is the chemical/physical composition of the adhesive itself that is used to create the seal. Accordingly, it is important to monitor the long term effectiveness of a prospective adhesive seal in order to determine not only the appropriate adhesive to use, but also the width of the bead or line of adhesive that should used to effectively seal, for example, a pair of thin glass plates or other such moisture-impermeable plates.

FIGS. 7 and 8 depict an arrangement that can be employed for such testing using the system and the mounting device 11 previously described. For this testing arrangement, a thin circular glass plate 101 about 0.15 cm thick is provided that has essentially the same dimensions as the standard composite film sample that is tested, namely a flat plate about 9 cm in diameter A large opening 103 is created centrally within the glass plate, which may be a circular or an oval hole. A thin glass disk 105, which may be of the same material of the plate, is provided. This disk 105 can, for instance, be a flat plate of circular shape having a diameter of about 5 cm, significantly less than the internal diameter of the cavity 25a, but substantially larger in diameter than the hole 103 so as to accommodate a bead of adhesive 107 between the glass disk and the plate around the hole, using a continuous line of adhesive of the same thickness as will be intended to be used in the perimeter seal of the cell phone or other display unit. The proportions are chosen to be such that such a line of adhesive 107 will have a defined length; for example, the circumference of a annular bead of adhesive sealing the disk 105 to the plate 101 may be the same length as the perimeter of the display unit of interest. The line of adhesive 107 should be uniform in width and have the specific width that is felt to be adequate for the desired barrier protection so that the thickness, the width and the length of the line of adhesive is the same as, or in a desired proportion to, that which will be used in the commercial device, e.g. 10 to 15 cm in length.

The assembly of plate, annular adhesive bead and disk is mounted in the mounting means 11, and when the system has reached the desired test temperature and the upstream and downstream chambers have been purged, it is ready for testing. A glass ampoule 89 is fractured so that the region on the upstream side of the circular plate 101 will be filled with the humid HTO vapor atmosphere which enters the region through the large hole 103. Thus, this humid atmosphere will be in contact with the upstream, i.e., interior, edge of the annular bead of adhesive 107. Accordingly, permeation into and slowly through the line of adhesive will occur, with the rate depending upon the physical characteristics of the adhesive material. The permeating HTO vapor will be collected by the slow flow of carrier gas through the downstream chamber 31 and carried to the radiation monitor as explained hereinbefore. Thus, the apparatus and system described hereinbefore with regard to testing the barrier properties of a thin film is thus equally useful for testing the barrier properties of an edge seal in an accurate manner for instances where the determination of even ultralow rates of permeation of moisture through such a seal is of significant importance.

Although the invention has been described with regard to certain preferred embodiments which constitute the best mode presently known to the inventors to carry out the invention, it should be understood that various changes and modifications as would be obvious to one having ordinary skill in this art can be made without departing from the scope of the invention which is defined by the claims that are appended hereto. Even though the primary working example is directed to testing improved barrier materials suitable for the formation of a flexible OLED or the like, it should be understood that other materials may alternatively be tested by appropriately altering the mounting device should such be found necessary. Although an RH of about 85% to 100% is preferably used, testing can be carried out at any RH desired by varying the amount of HTO in the glass ampoule used. Disclosures of all previously enumerated U.S. patents and patent applications are expressly incorporated herein by reference. Particular features of the invention are enumerated in the claims which follow.

The invention claimed is:

1. A method for measuring ultralow moisture permeation through a sample at a temperature substantially above ambient using a radioactive compound, which method comprises the steps of:

heating the sample being measured to a desired test temperature substantially above ambient, providing a first controlled access region adjacent an upstream surface of the sample, providing a second controlled access region adjacent to a downstream surface of the sample, supplying a defined amount of radioactive gas sufficient only for a single test to the first region at predetermined relative humidity at said test temperature so as to be in contact with the upstream surface of the sample, said radioactive gas being provided in a sealed glass ampoule and supplied by fracturing said glass, collecting radioactive gas permeating from the downstream surface of the sample by circulating a very slow flow of dry carrier gas through the second region to provide a radioactive stream, flowing said radioactive stream from said second region to an ionization chamber containing a beta-particle radiation monitor, continuously monitoring said stream in said ionization chamber to detect the presence of beta-particles emitted by the amount of said radioactive gas which permeates through the sample and generating signals reflective thereof, and receiving said signals from said radiation monitor and converting the signals to calculate the permeation rate through the sample, whereby the sensitivity of the method allows for measurement of permeation of moisture at a rate of 0.001 gm or less/m²/day, and continuing such operation at said test temperature over a period of at least about 2 days to attain a substantially steady state of moisture permeation for the sample, whereby the barrier performance of the sample for at least one month can be assessed from said steady state measurement.

2. The method for measuring permeation according to claim 1 wherein said first region is first purged of moisture, and following fracturing of said glass, said volume of said first region is of such a size that the amount of HTO vapor from said ampoule creates a precise RH and so that the pressure is substantially equal to the pressure in said second region.

3. The method for measuring permeation according to claim 1 wherein said sample is an annular bead of sealant fixed between two spaced-apart moisture-impermeable surfaces.

4. The method for measuring permeation according to claim 1 wherein said radioactive gas is tritiated water vapor (HTO) and said carrier gas is dry methane.

5. The method for measuring permeation according to claim 4 wherein a relative humidity of HTO between about 85% and 100% is supplied to the first region throughout the entire test period for the sample.

6. The method for measuring permeation according to claim 1 wherein said sample is a sheet of polymeric film which carries a barrier coating comprising at least one layer of inorganic material.

7. The method for measuring permeation according to claim 6 wherein said sheet is heated without restraint to about said elevated temperature and is then clamped about a perimeter of a test region so as to close said first region prior to supplying said radioactive gas.

8. The method for measuring permeation according to claim 1 wherein said first region includes a subregion to which a defined amount of HTO is provided by said fracturing of said sealed ampoule which contains radioactive HTO vapor.

9. The method for measuring permeation according to claim 8 wherein the amount of specific radioactivity of HTO in said first region is not greater than about 10 millicuries.

10. The method for measuring permeation according to claim 9 wherein said carrier gas enters said second region at a pressure just sufficient to maintain said very slow flow, which flow is so limited in radiation level that it may be safely vented to the atmosphere following said monitoring in said ionization chamber.

11. Apparatus for measuring ultralow permeation through a sample of barrier material, which apparatus comprises:

means to heat the sample to a test temperature substantially above ambient, means for mounting the sample to provide controlled access to an upstream surface of the sample via a first chamber and controlled access to a downstream surface thereof via a second chamber, while said sample and said chambers are at said test temperature, means for supplying a defined amount of radioactive gas to said first chamber sufficient only for a single test, where it will be in contact with the upstream surface of the sample, which radioactive gas supply means comprises a subchamber that includes a passageway which receives a glass ampoule containing HTO having a radioactivity not greater than about 10 millicuries, which subchamber is interconnected with said first chamber, and means for opening said receptacle in the form of a slidable tool which can be moved to fracture the glass ampoule to supply said HTO vapor throughout said first chamber when desired, means for circulating a very slow flow of carrier gas through said second chamber to provide a radioactive exit stream containing the gas permeating from the downstream surface of the sample, conduit means for directing said exit stream from said second chamber to an ionization chamber, a radiation monitor in said ionization chamber for continuously monitoring said exit stream to detect radioactivity and for creating signals indicative of radioactivity monitored, and conversion means for receiving signals from said radiation monitor and converting the signals to measurements of permeation rate of moisture through the sample which may be as low as $1 \times 10^{-6}$ gm per sq. meter per day, whereby continuous measurement of said exit stream for permeation at a temperature which is at least about twice ambient temperature allows prediction of long term barrier performance of the sample.

12. The apparatus for measuring ultralow permeation according to claim 11 wherein said supply means also includes means to balance the pressures to avoid any significant pressure differential between said first and second chambers and to provide a relative humidity of tritiated water vapor (HTO) between about 95% and 100% throughout the entire test period for a sample.

13. The apparatus for measuring permeation according to claim 11 which further comprises means for removing all humidity from said first chamber prior to opening said receptacle to supply HTO vapor as said radioactive gas.

14. The apparatus for measuring ultralow permeation according to claim 11 which includes one said ampoule that contains from about 0.001 to about 0.01 cc of HTO.

15. The apparatus for measuring ultralow permeation according to claim 11 wherein said mounting means will support a thin sheet of polymeric film that includes at least one barrier layer.

16. The apparatus for measuring ultralow permeation according to claim 11 wherein said mounting means will support a plate of substantially moisture-impervious material having a generally central aperture, which plate carries an annular bead of sealant surrounding said aperture, which bead is also attached to a facing parallel surface that is similarly impervious.

17. A method for measuring ultralow moisture permeation through a sample using a radioactive compound so as to provide an indication of the sample's character as a long term baffler to moisture permeation, which method comprises the steps of:

heating the sample to a desired test temperature substantially above ambient in a heated enclosure where there is controlled access to an upstream surface of the sample in a first region and controlled access to a downstream surface thereof in a second region, supplying a defined amount of radioactive HTO vapor to the first region at predetermined relative humidity at said test temperature by fracturing a glass ampoule containing from about 0.001 to about 0.01 cc of HTO so as to provide radioactive HTO sufficient only for a single test which will be in contact with the upstream surface of the sample, collecting said radioactive gas which permeates from the downstream surface of the sample by circulating a very slow flow of dry carrier gas through the second region to provide a radioactive stream, flowing said radioactive stream exiting from said second region to an ionization chamber containing a beta-particle radiation monitor, continuously monitoring said exit stream in said ionization chamber with high sensitivity to detect ionization indicative of beta particles emitted by HTO which permeates through the sample and generating signals reflective thereof, receiving said signals from said radiation monitor and converting the signals into calculation of the permeation rate through the sample which may be as low as $1 \times 10^{-6}$ gm/m$^2$/day, and continuing such operation at said test temperature over a period of at least about 2 days while plotting changes in the calculated rates until increases are no longer occurring and a substantially steady state of moisture permeation is shown as having been attained by the sample, which steady state values permits the barrier performance of the sample for one month or more to be assessed.

* * * * *

UNITED STATES PATENT AND TRADEMARK OFFICE
CERTIFICATE OF CORRECTION

PATENT NO. : 7,257,990 B2
APPLICATION NO. : 11/114814
DATED : August 21, 2007
INVENTOR(S) : Bujas et al.

It is certified that error appears in the above-identified patent and that said Letters Patent is hereby corrected as shown below:

Column 13, line 2, delete "baffler" and insert --barrier--.

Signed and Sealed this

Eighth Day of April, 2008

JON W. DUDAS
*Director of the United States Patent and Trademark Office*